United States Patent
Ripart

(10) Patent No.: US 6,625,491 B2
(45) Date of Patent: Sep. 23, 2003

(54) ACTIVE IMPLANTABLE MEDICAL DEVICE, IN PARTICULAR A PACEMAKER, DEFIBRILLATOR AND/OR CARDIOVERTOR OF THE MULTISITE TYPE, CAPABLE OF DETECTING INDUCED TACHYCARDIA

(75) Inventor: Alain Ripart, Gif sur Yvette (FR)

(73) Assignee: ELA Medical S.A., Montrouge (FR)

( * ) Notice: Subject to any disclaimer, the term of this patent is extended or adjusted under 35 U.S.C. 154(b) by 111 days.

(21) Appl. No.: 09/728,130

(22) Filed: Dec. 1, 2000

(65) Prior Publication Data

US 2001/0005790 A1 Jun. 28, 2001

(30) Foreign Application Priority Data

Dec. 2, 1999 (FR) .............................. 99 15220

(51) Int. Cl.[7] .............................................. A61N 1/368
(52) U.S. Cl. .............................. 607/15; 607/14; 607/27; 600/518
(58) Field of Search ................ 607/15, 9, 14, 607/27, 4, 5; 600/518

(56) References Cited

U.S. PATENT DOCUMENTS

| | | | | |
|---|---|---|---|---|
| 4,830,006 A | * | 5/1989 | Haluska et al. ................ 607/12 |
| 5,507,783 A | * | 4/1996 | Buchanan ................... 600/518 |
| 5,514,161 A | | 5/1996 | Limousin ...................... 607/9 |
| 5,983,138 A | | 11/1999 | Kramer ......................... 607/9 |
| 5,995,870 A | | 11/1999 | Cazeau et al. ................ 607/9 |
| 6,185,459 B1 | * | 2/2001 | Mehra et al. ................ 607/14 |

FOREIGN PATENT DOCUMENTS

| | | | | |
|---|---|---|---|---|
| EP | 0676 216 A1 | 4/1995 | .......... A61N/1/368 |
| EP | 0 813 889 A2 | 12/1997 | .......... A61N/1/368 |
| EP | 0 862 927 A1 | 9/1998 | .......... A61N/1/365 |
| EP | 0 813 889 A3 | 11/1998 | .......... A61N/1/368 |
| EP | 0 935 979 A1 | 8/1999 | ............ A61N/1/37 |

* cited by examiner

Primary Examiner—Kennedy Schaetzle
(74) Attorney, Agent, or Firm—Orrick, Herrington & Sutcliffe LLP

(57) ABSTRACT

An active implantable medical device, in particular a pacemaker, defibrillator and/or cardiovertor of the multisite type, capable of detecting an induced tachycardia. Such a device is to be coupled to electrodes placed in at least two cardiac sites of the same cardiac chamber type, e.g., at least two ventricular sites, right and left, at least two atrial sites, right and left, or at least two sites of the same cavity (atria or ventricular). The device has a cardiac signal collection circuit to detect a depolarization potential, and a stimulation circuit to apply stimulation pulses to at least certain of the aforesaid sites. The device monitors the heart rate, detects suspicion of an induced tachycardia condition, operating in response to the heart rate and determines the presence of an induced tachycardia condition if the heart rate exceeds a predetermined threshold for a length of time greater than a predetermined threshold, and temporarily modifies the operation of the device in the event of the detection of an induced tachycardia condition to cause the induced tachycardia condition to disappear.

5 Claims, 3 Drawing Sheets

ACTIVE IMPLANTABLE MEDICAL DEVICE, IN PARTICULAR A PACEMAKER, DEFIBRILLATOR AND/OR CARDIOVERTOR OF THE MULTISITE TYPE, CAPABLE OF DETECTING INDUCED TACHYCARDIA

FIELD OF THE INVENTION

The present invention relates to "active implantable medical devices" as such devices are defined by the Jun. 20, 1990 directive 90/385/CEE of the Council of the European Communities, more particularly to pacemaker, defibrillator and/or cardiovertor devices which are able to deliver to the heart stimulation pulses of low energy for the treatment of cardiac rate disorders, and even more particularly to the so-called "multisite" prostheses, in which electrodes are placed in a plurality of distinct respective sites in the tissue.

BACKGROUND OF THE INVENTION

Multisite prosthesis typically comprise at least one ventricular site and one atrial site, and are known as "double chamber" (right atrial stimulation and right ventricular stimulation) or, more generally, "triple chamber" (right atrial stimulation and double ventricular stimulation) or "quadruple chamber" (double atrial stimulation and double ventricular stimulation) prosthesis. Multisite devices also include a prosthesis type which provides stimulation at two distinct sites in the same cavity, for example, a double stimulation of the left ventricle.

In addition to the treatment of cardiac rate disorders, it has been proposed to treat by stimulation disorders of the myocardial contraction, which are observed among patients having a cardiac insufficiency. These disorders may be spontaneous or induced by a traditional stimulation. One will be able in particular to refer to the study of J. C. Daubert et al., Stimucoeur, 25, n°3, pp. 170–176 which gives a report on this subject. Daubert et al. proposed to stimulate simultaneously and permanently the left and right ventricles, for the re-synchronization of both ventricles. One often can observe spectacular results for patients having a Class III-type cardiac insufficiency, whose condition was not significantly, if at all, improved by the traditional treatments.

In the following discussion, the case of a stimulation of the lower cardiac cavities, i.e., the case of a double ventricular stimulation, is discussed because this case is the one which is the most unfavorable for the cardiac function of the patient. The mechanism which will be described can, however, affect in the same way, the upper cardiac cavities, and the solutions suggested could be applied mutatis mutandis to a double atrial stimulation.

After delivery of a stimulation pulse, a depolarization wave is propagated in the volume of the myocardium around the stimulation point. A consequence of this stimulation is the creation, after the passage of the wave, of a refractory period (about 250 ms). During the refractory period, the cardiac cells are no longer excitable and thus will not respond to a stimulation. This refractory period is followed, before the cardiac cells have returned to the normal state, by a transient period during which the cardiac cells are hyperexcitable. Thus, any stimulation falling into this transient period, whether of a natural (spontaneous) or a stimulated (induced) origin, can trigger the excitation state of a cardiac cell and another depolarization wave due to the electric instability of the cardiac cells, and thus generate an undesirable phenomenon of tachycardia, i.e., an abnormally high cardiac rate.

Another phenomenon owing to the operation of the multisite device is that stimulation which is simultaneous or with a slight delay on two or more sites can lead to the creation of areas presenting aberrations of the electrical conduction in the region where the two depolarization propagating waves meet. This can lead to the appearance of a zone known as a "block", in which the propagation of the depolarization wave will be slowed down, and perhaps even stopped.

In addition, a double atrial stimulation can generate the following phenomenon: the first stimulation will lead, by normal conduction, to the subsequent depolarization of the ventricle; the second stimulation, whose propagation will be delayed in the zone of the block, also will reach the ventricle, but, because of the delay, will reach the ventricle during a point in time when the atrium is no longer in its refractory period, and thus will cause an undesirable contraction involving a disorder of the cardiac rate which can result in a tachycardia crisis.

SUMMARY OF THE INVENTION

It is, therefore, an object of the present invention to overcome these various phenomena known as "induced tachycardia," or "reentry tachycardia" (collectively designated as "TRE") and pacemaker mediated tachycardia ("PMT") which can be caused by multisite type cardiac stimulation devices such as pacemakers.

To this end, the present invention broadly concerns a device of the multisite type, i.e., in which electrodes are to be placed in at least two cardiac sites of the same chamber type, such as at least two ventricular sites, one right and one left, or in at least two atrial sites, one right and one left, or in at least two sites of the same cavity, or combinations thereof. The electrodes are to be connected to a cardiac signal collection circuit to detect a depolarization potential, as well as to a stimulation circuit which delivers stimulation pulses to at least certain of the aforesaid sites.

According to one aspect of the invention, the device comprises means for monitoring the heart rate, means for detecting an induced tachycardia condition, operating in response to the monitoring means, to detect the presence of an induced tachycardia if the heart rate exceeds a predetermined threshold for a length of time greater than a predetermined threshold, and means for temporarily modifying the operation of the device in the event of a detected induced tachycardia condition.

In a preferred embodiment, the detection means detects the presence of an induced tachycardia only if the heart rate has a rate of increase which exceeds a predetermined minimal value.

Modifying the operation of the device can advantageously be implemented by reducing the time of a stimulation delay that may exist between the two cardiac sites, e.g., the two ventricular sites (right and left), and/or the two atrial sites (right and left), and/or the two stimulation sites of the same cavity.

In the alternative or in addition, the modifying the operation of the device may inhibit the stimulation of at least one of the two cardiac sites, e.g., one of the right and left ventricular sites, and/or one of the two right and left atrial sites, and/or one of the two stimulation sites of the same cavity.

Advantageously, one can foresee that modifying the operating mode to inhibit the delivery of a stimulation pulse is preferably employed only after having attempted to reduce the time of the stimulation delay, which reduction was followed by the case of a persistent tachycardia.

Preferably after activation of the means to modify the operation of the device, the modification is maintained activated for a predetermined length of time, and then deactivated.

Advantageously, one can foresee that after a deactivation of the operation modifying means, the normal operating mode of the device (i.e., normal or preselected mode of operation in the absence of an induced tachycardia condition) is reactivated (i.e., restored). Then, in the event of a new detection of induced tachycardia condition, the operation modifying means will again be employed to modify the operation of the device as described so as to inhibit a persistence of the induced tachycardia condition.

BRIEF DESCRIPTION OF THE DRAWINGS

Other characteristics, features and advantages of the invention will appear to the person of ordinary skill in the art in view of the following detailed description of a preferred embodiment, made with reference to the annexed drawing figures, which.

DETAILED DESCRIPTION OF THE INVENTION

Figure 1:
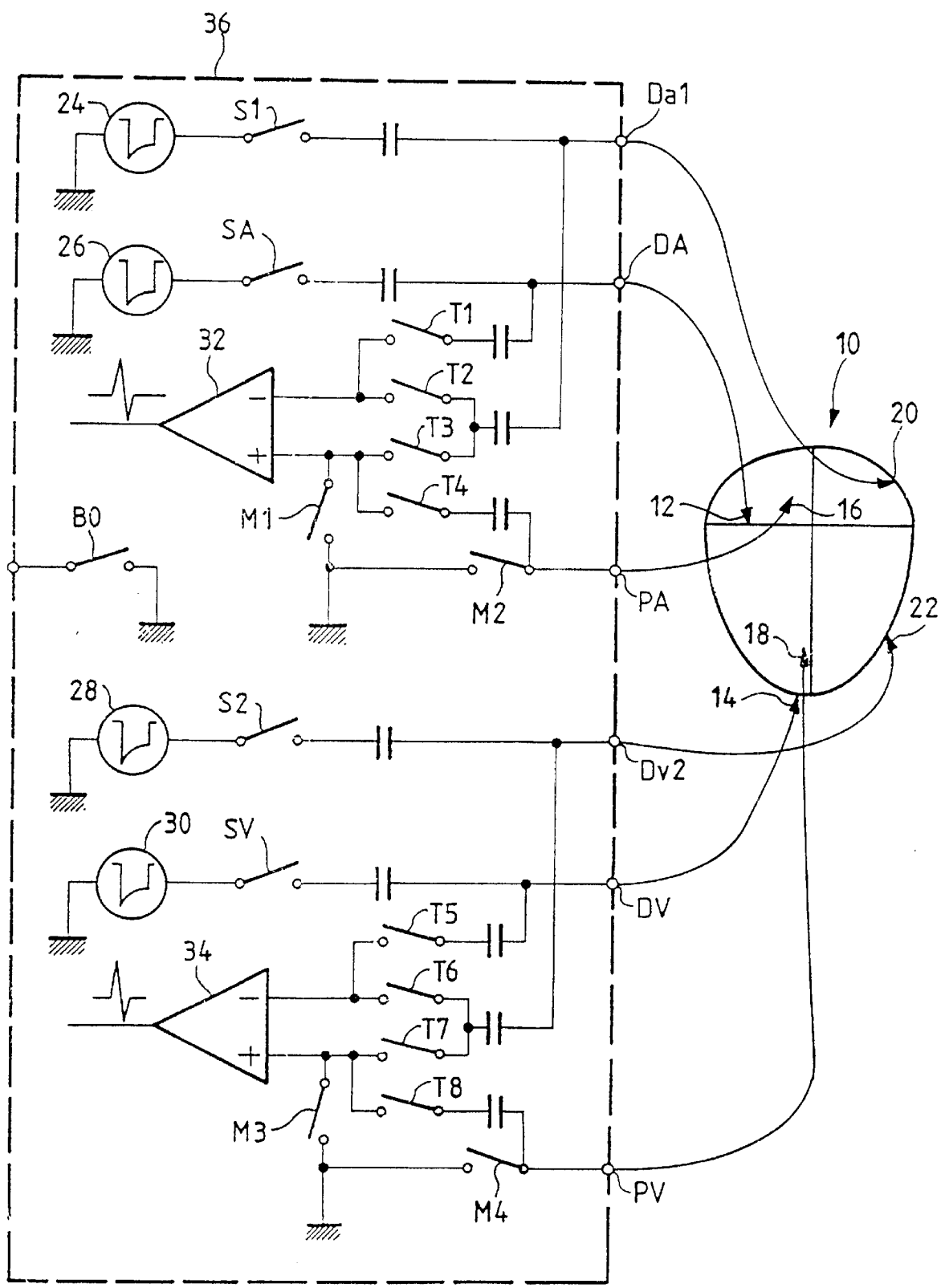
FIG. 1 is a schematic diagram of a pacemaker realized according to teaching of the present invention, and a plurality of leads implanted in various sites of a myocardium.

With reference to FIG. 1, the drawing of U.S. application Ser. No. 09/218,678, now U.S. Pat. No. 6,253,106, the reference 10 designates, schematically and in a general manner, the myocardium, on which are implanted various leads in a plurality of sites 12, 14, 16, 18, 20 and 22. It is preferred that the electrodes are in effective contact with the myocardium, such that each of electrodes 12, 14, 20 and 22 is in contact with each of the four cavities of the myocardium. It also is preferred to have, in addition, floating electrodes, such as electrodes 16 and 18, which can be used to serve as reference potentials to detect signals or to stimulate, when the stimulation is operated in a bipolar mode. These floating electrodes can be, for example, constituted by the proximal electrode of a bipolar lead, the distal extremity of which is in contact with the cavity.

Thus, in the configuration of electrodes illustrated on the FIG. 1, electrodes 12 and 16 are those of a bipolar lead implanted in the right atrium, electrodes 14 and 18 are the ones of a bipolar lead implanted in the right ventricle, the electrode 20 is the one of a unipolar lead implanted in the left atrium, and the electrode 22 is the one of a unipolar lead implanted in the left ventricle.

This configuration is, however, in no manner meant to be restrictive concerning the number of electrodes, as well as the manner of their configuration. Furthermore, the leads (electrodes in contact with the myocardium or floating electrodes), need not necessarily be placed in cardiac cavities, but also can be situated in sites which allow one to stimulate cavities in an indirect manner. For example, leads implanted in a coronary sinus, or alternately at the exterior of the myocardium (e.g., an epicardial lead) can be used. It is possible even to place all electrodes in the same cavity, for example, in the right ventricle, with one electrode located in the septum such that it would be able to stimulate the left ventricle, and/or with an electrode the separation wall of cavities, etc.

Concerning the pacemaker, in the illustrated example, it comprises (here again, in a nonrestrictive manner) four independent poles, allowing each pole to deliver an electrical stimulation, which is programmable in amplitude and in width, to four points of the heart, and two poles, typically of proximal electrodes, serving as reference potentials for the stimulation and the detection. By convention, the six poles of the device are designated according to a typical utilization as illustrated, although this constitutes in no case a limit to the various possibilities of the system, since each of the poles can be connected to a site situated in any cardiac cavity.

One will designate the poles as follows:

DA and DV (Distal Atrial and Distal Ventricular), the poles connected to electrodes 12 and 14, PA and PV (Proximal Atrial and Proximal Ventricular), the poles connected to electrodes 16 and 18, Da1 (Distal atrial). the pole connected to the electrode 20, that is the first additional pole (No. 1) as compared to a double chamber device, and Dv2 (Distal ventricular) the pole connected to the electrode 22, that is the second additional pole (No. 2) as compared to a double chamber device.

The pacemaker comprises four stimulation stages 24, 26, 28 and 30 and two detection circuits, with respective amplifiers 32 and 34.

Various electronic switches SA, SV, S1, S2, M1–M4 and T1–T8 are connected in the manner represented on the figure between stages of stimulation 24, 26, 28 and 30, and stages of detection 32 and 34, on the one hand, and the six poles DA, PA, Da1, DV, PV, Dv2, on the other hand. They allow a further connection of the these six poles to each of stages 24 to 34, so as to realize various stimulation configurations and various configurations for the detection of the cardiac signal.

It also is foreseen to have a switch B0 allowing one to connect the metallic case 36 of the device to the ground of the system electronics, when one wishes to realize a stimulation or a detection between a endocardiac pole and the ground of the case.

Set forth below are various stimulation and detection configurations that can be realized by means of these different switches. The various modes of detection and stimulation will be designated as follows:

"unipolar detection" ("Det. unip.") is a detection between an endocardiac pole and the case, "bipolar detection" ("Det. bip.") is a differential detection between two endocardiac poles (the case constituting a reference for the common mode), "tripolar detection" ("Det. trip.") is a detection on two endocardiac poles connected between them, referenced to a third endocardiac pole (the case constituting a reference for the common mode), "unipolar stimulation" ("Stim. unip.") is a stimulation between an endocardiac pole and the case, "bipolar stimulation" ("Stim. bip.") is a stimulation between two endocardiac poles of which one is at ground (case not connected).

In the case of a classic DDD pacemaker (double chamber), the term "bipolar" ("bip.") refers to two endocardiac poles situated in the same cavity, but in the case of a multisite pacemaker (MS), this is no longer the case. One will call by convention "quasi-bipolar" ("quasi-bip.") a configuration with two endocardiac electrodes in two different cavities, and similarly for "quasi-tripolar" ("quasi-trip."). The different possibilities of configuration are given by the following Table, that indicates: (1) the configuration considered, (2) poles (electrodes) implied, (3) the fact that it concerns an already known configuration such as in a classic double chamber (DDD) pacemaker, or a new configuration, specific to the multisite (MS) device of the present invention, (4) switches to be closed, and (5) switches to be opened.

| Table | Configuration | Type | Closed | Open |
|---|---|---|---|---|
| Det.unip | Da1 | MS | B0, M1, T2 | M2, T1, T3, T4 |
| Det.quasi-bip. | Da1/PA | MS | B0, T2, T4 | M1, M2, T1, T3 |
| Det.quasi-bip. | DA/Da1 | MS | B0, T1, T3 | M1, M2, T2, T4 |
| Det.quasi-trip. | [DA+Da1]/PA | MS | B0, T1, T2, T4 | M1, M2, T3 |
| Det.bip. | DA/PA | DDD | B0, T1, T4 | M1, M2, T2, T3 |
| Det.unip. | DA | DDD | B0, M1, T1 | M2, T2, T3, T4 |
| Stim.unip. | Da1 | MS | B0, S1 | M2, M4 |
| Stim.quasi-bip. | Da1/PA | MS | M2, S1 | B0, M4 |
| Stim.unip. | DA | DDD | B0, SA | M2, M4 |
| Stim.bip. | DA/PA | DDD | M2, SA | B0, M4 |
| Det.unip. | Dv2 | MS | B0, M3, T6 | M4, T5, T7, T8 |
| Det.quasi-bip. | Dv2/Pv | MS | B0, T6, T8 | M3, M4, T5, T7 |
| Det.quasi-bip. | DV/Dv2 | MS | B0, T5, T7 | M3, M4, T6, T8 |
| Det.quasi-trip. | [DV+Dv2]/PV | MS | B0, T5, T6, T8 | M3, M4, T7 |
| Det.bip. | DV/PV | DDD | B0, T5, T8 | M3, M4, T6, T7 |
| Det.unip. | DV | DDD | B0, M3, T5 | M4, T6, T7, T8 |
| Stim.unip. | Dv2 | MS | B0, S2 | M2, M4 |
| Stim.quasi-bip. | Dv2/PV | MS | M4, S2 | B0, M2 |
| Stim.unip. | DV | DDD | B0, SV | M2, M4 |
| Stim.bip. | DV/PV | DDD | M4, SV, | B0, M2 |

One will appreciate from the foregoing table that there are shown—but in a non exhaustive manner, eight different stimulation configurations and twelve possible detection configurations.

In practice, the selection of the location of the electrodes in the various parts of the four cardiac cavities is left to the choice of the medical practitioner.

The configurations of stimulation and detection are thus realized, either according to the indications (selections) of the medical practitioner, or in an automatic manner, by research of the preferential configuration. Thus, switches can be programmed (e.g., using a suitable software program) in a manner as to modify dynamically the configuration during the functioning of the pacemaker, so as to adapt dynamically the pacemaker in order to be in the best configuration. In this regard, the configuration is considered as "best" if it obtains an improvement of a cardiac parameter, such as the flow rate (relating to the performance obtained by the other possible configuration). The automatic research can be initiated on a periodic basis, on a prompt from a medical practitioner using a remote programmer. Reference in this regard is made to EP 0862927 and its corresponding U.S. Pat. No. 5,995,870, which are commonly assigned with the invention hereof.

Stimulation on each of the four chosen poles are controlled by a certain number of parameters, notably delays, as follows:
   delay between stages, namely between the atrial stage A and the ventricular stage V, by the atrio-ventricular delay which is well known in a DDD pacemaker,
   delay between cavities of the same stage, namely between DA and Da1 or between DV and Dv2, delay DA-Da1 and DV-Dv2 also being able, following the suitable programming of the pacemaker, to be reversed, namely delays Da1-DA or Dv2-DV, subsequent to the location of leads in the heart, that the medical practitioner will have to specify at the implantation of the device, a certain number of new preferential modes of stimulation which are proposed, accompanied by programmable parameters of temporal coupling.

Delays between stages, and similarly delays between cavities, can be, for example, programmable values of from 0 to 300 ms, preferably by steps of 8 ms (related to the microprocessor clock cycle). For each pole that is able to deliver an electrical stimulation, the parameters of the stimulus amplitude are accessible in an independent manner as are well known. It should be understood that the various switches are programmable under software control, using known electronic circuit structures and techniques as are known to persons of ordinary skill in the art.

The research for the optimal or best configuration can be manual or automatic, such that the device can be sequenced through the range of possible configurations until the optimal or best is determined, and then selected by appropriate setting of the plurality of switches. The parameter to be optimized can be measured by the implanted device or in conjunction with a remote programmer or remote monitoring equipment coupled to the patient.

The device thus provides, in a known manner, the continuous monitoring of cardiac signals and determination of the heart (or cardiac) rate (or frequency).

Figure 2:
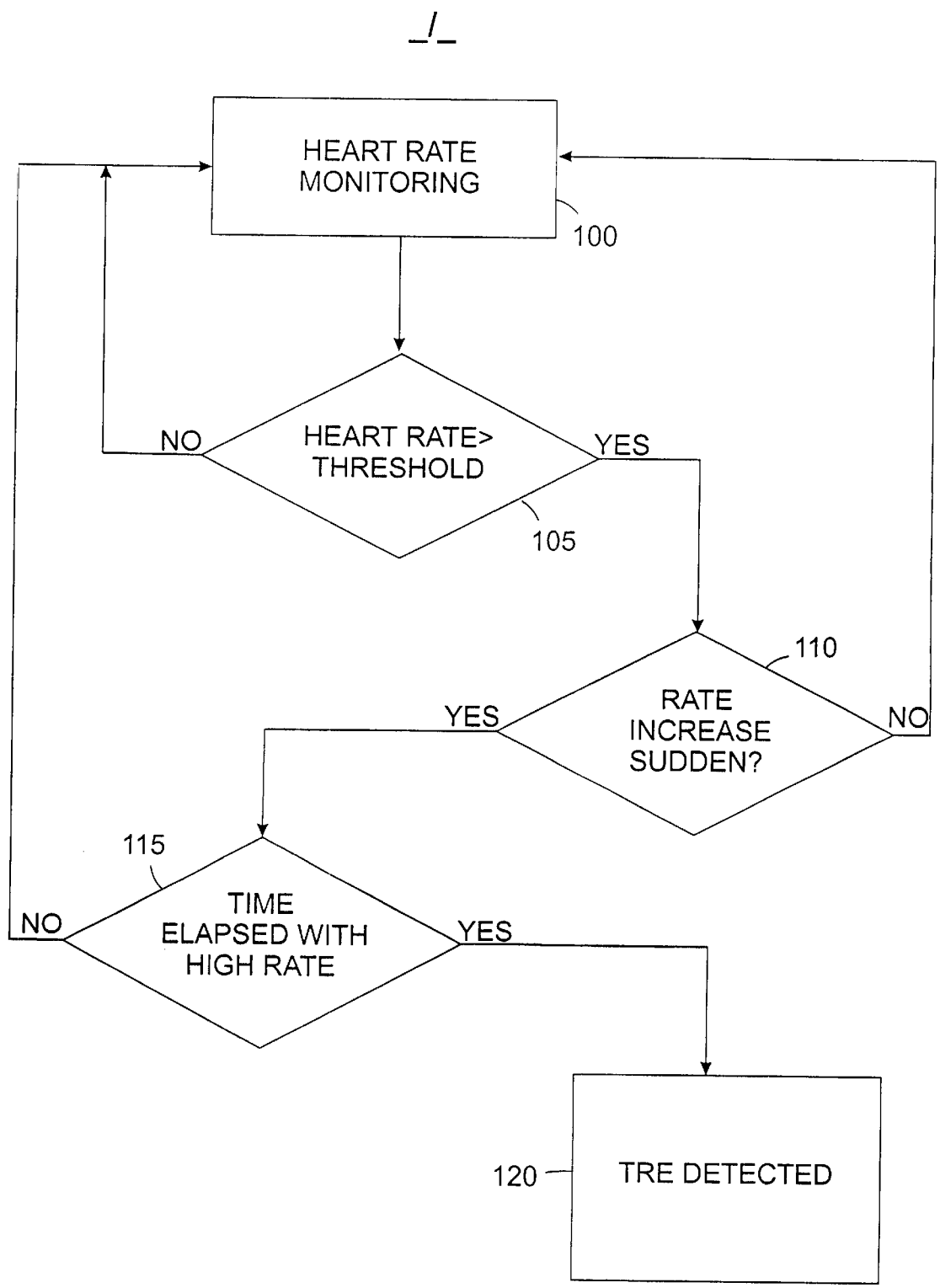
FIGS. 2 and 3 are flow charts of a process in accordance with a preferred embodiment of the invention.

Referring now to FIG. 2, if the rate detected at stage 100 is determined to exceed a certain threshold (for example, 120 bpm) at stage 105, the device then enters an investigatory phase referred to as a suspicion of induced tachycardia at stage 115. Apart from the determined rate exceeding the threshold, preferably for a minimum period of time, an additional criterion may be applied at stage 110 to establish this suspicion phase, namely the evaluation of the rate of increase in the cardiac frequency. If the frequency increases relatively slowly, it can be assumed to be a physiological variation, for example, a physiological response to an increase in patient activity, also known as an "effort" performed by the patient. On the other hand, if the increase in frequency is sudden, the assumption that the change is due to an induced tachycardia is more plausible.

After the phase of suspicion is reached, the device enters a phase of confirmation of the induced tachycardia at stage 115. In this case, there is confirmation if the determined heart rate is maintained above the considered threshold during a programmable interval of predetermined time, for example, during more than one minute.

If such is not the case, i.e., if the heart rate falls below the considered threshold value, the device does not undertake any modification of its normal mode of operation, and continues the monitoring of the heart rate at stage 100, waiting for a new suspicion of induced tachycardia to occur.

Figure 3:
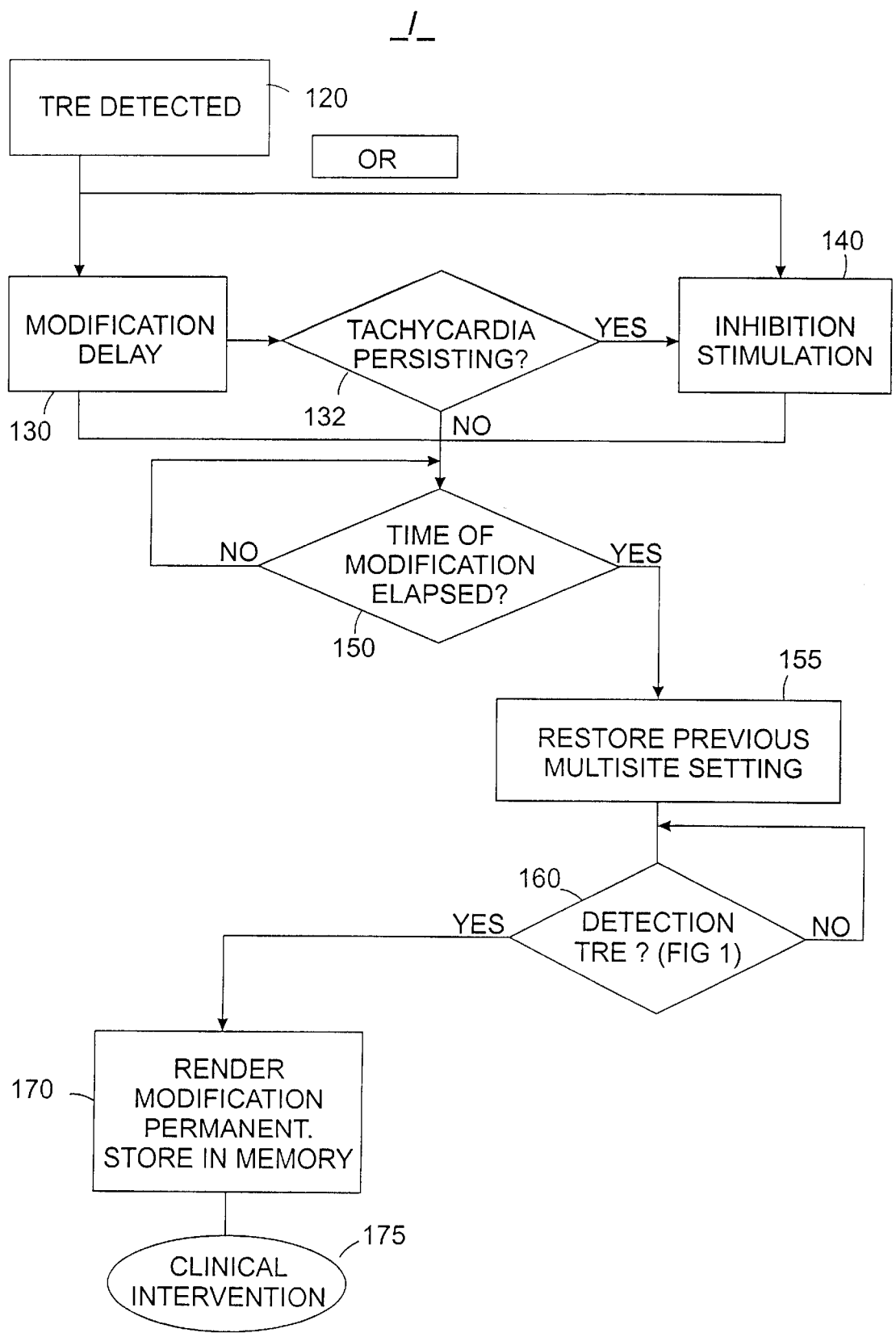

In the event of confirmation of an induced tachycardia at stage 120, with reference now to FIG. 3, the device then modifies its operation so as to try to make the induced tachycardia condition disappear.

First, if the normal operating mode is one of simultaneous stimulation, the device tries at stage 130 to reduce any stimulation delay which may exist between the at least two cardiac sites of the same chamber type being stimulated, for example, the two ventricles, or the two atria, or between the two sites of the same cavity that is stimulated at several points.

If the induced tachycardia persists at stage 132 despite the reduction of the stimulation delay, in the preferred embodiment the device then inhibits stimulation on some of the sites at stage 140. For example, the device can inhibit the stimulation of the left ventricle in the case of a ventricular stimulation, or inhibit stimulation of one of the sites if the same cavity is stimulated at several points.

If the induced tachycardia ceases after one or both of these modifications of operation, one can advantageously foresee that the device makes another attempt to operate in its initial or normal multisite stimulation mode later on at stage 155, for example, after spending several days in the modified configuration (stage 150).

In one embodiment, in the event of a reappearance of a confirmed induced tachycardia phenomenon at stage 160, the device will thereafter maintain the modified operation configuration until at stage 170 a subsequent intervention is made by a clinician at stage 175.

It should be understood that these various events, such as the moment (date and time) of their respective appearances, can of course be recorded in the memory of the device, according to known methods, for later consultation by telemetry transmission of suitable event makers to a remote programmer.

The preferred embodiment of the invention is implimented in a software routine for controlling the aforementioned multisite device to perform the functions recited herein. One skilled in the art will appreciate that the present invention can be practiced by other than the described embodiments, which are presented for the purposes of illustration and not of limitation.

I claim:

1. An implantable pacemaker, defibrillator and/or cardiovertor of the multisite type, for use with electrodes placed in at least two sites of the same chamber type, selected from among the group consisting of right and left ventricular sites, right and left atrial sites, and two sites of the same cavity, said multisite type device having a cardiac signal collection circuit to detect a depolarization potential at one of said sites, a stimulation circuit to apply stimulation pules to at least certain of said foregoing at least two sites, and a first mode of multisite stimulation operation, comprising:

means for monitoring depolarization signals and determining a heart rate;

means for comparing the determined heart rate to a first predetermined threshold;

means for detecting an induced tachycardia condition, in response to the comparing means determining that the heart rate exceeds the first predetermined threshold for a length of time, said length of time being greater than a second predetermined threshold; and means for temporarily modifying said first mode of operation of the device for a predetermined length of time in response to said detected induced tachycardia condition and thereafter restoring the device operation to its first mode of operation, and in response to a subsequent determination of an induced tachycardia condition, modifying the first mode of operation in a semi-permanent manner.

2. The device of claim 1, wherein the detecting means further comprises means for determining a rate of increase of the heart rate, means for comparing the determined rate of increase in the heart rate to a predetermined minimal value, and means for confirming an induced tachycardia condition in response to the determined rate of increase of the heart rate exceeds a predetermined minimal value.

3. The device of claim 1, wherein the operation modifying means further comprises means for reducing a delay of stimulation between said at least two sites of the same cardiac chamber type.

4. The device of claim 3, wherein the operation modifying means further comprises means for inhibiting the stimulation of one of said at least two sites of the same cardiac chamber type and wherein the means for inhibiting the stimulation of one of said two sites is activated only after said means for reducing the delay of stimulation has reduced said delay, followed by a detected induced tachycardia condition.

5. The device of claim 1, wherein the operation modifying means further comprises means for inhibiting the stimulation of one of said at least two sites of the same cardiac chamber type.

* * * * *

UNITED STATES PATENT AND TRADEMARK OFFICE
CERTIFICATE OF CORRECTION

PATENT NO.    : 6,625,491 B2
DATED         : September 23, 2003
INVENTOR(S)   : Alain Ripart It is certified that error appears in the above-identified patent and that said Letters Patent is hereby corrected as shown below:

Column 2,
Line 57, delete "modifying" and insert -- modifications to -- therefor;

Column 4,
Line 33, delete "the these" and insert -- these -- therefor;
Line 40, delete "a endocardiac" and insert -- an endocardiac -- therefor;

Column 5,
Line 57, delete "poles are" and insert -- poles is -- therefor; and

Column 7,
Line 37, delete "stimulation pule's" and insert -- stimulation pulses -- therefor.

Signed and Sealed this

Sixteenth Day of August, 2005

JON W. DUDAS
*Director of the United States Patent and Trademark Office*